(12) United States Patent
Wahlquist

(10) Patent No.: US 8,426,700 B2
(45) Date of Patent: Apr. 23, 2013

(54) GARDEN BEAN SB4474

(75) Inventor: Daniel James Wahlquist, Nampa, ID (US)

(73) Assignee: Syngenta Participations AG, Basel (CH)

( * ) Notice: Subject to any disclaimer, the term of this patent is extended or adjusted under 35 U.S.C. 154(b) by 218 days.

(21) Appl. No.: 13/034,753

(22) Filed: Feb. 25, 2011

(65) Prior Publication Data

US 2012/0222144 A1 Aug. 30, 2012

(51) Int. Cl.
*A01H 5/00* (2006.01)
*A01H 5/10* (2006.01)
*A01H 1/00* (2006.01)
*A01H 4/00* (2006.01)
*C12N 15/82* (2006.01)

(52) U.S. Cl.
USPC ........... 800/313; 800/260; 800/279; 800/288; 800/300; 800/302; 800/278; 800/265; 435/410; 435/421

(58) Field of Classification Search .................. None
See application file for complete search history.

(56) References Cited

U.S. PATENT DOCUMENTS 7,645,924 B2 * 1/2010 Gehin .......................... 800/313

* cited by examiner

*Primary Examiner* — Stuart F Baum
(74) *Attorney, Agent, or Firm* — Karen Magri; Syngenta Participations AG

(57) ABSTRACT

A novel garden bean cultivar, designated Ambition, is disclosed. The invention relates to the seeds of garden bean cultivar Ambition, to the plants of garden bean line Ambition and to methods for producing a garden bean plant by crossing the cultivar Ambition with itself or another garden bean line. The invention further relates to methods for producing a garden bean plant containing in its genetic material one or more transgenes and to the transgenic plants produced by that method and to methods for producing other garden bean lines derived from the cultivar Ambition.

24 Claims, No Drawings

GARDEN BEAN SB4474

FIELD OF THE INVENTION

The present invention relates to a new and distinctive Garden Bean (*Phaseolus vulgaris*) cultivar, designated SB4474, also referred to herein as 'Ambition'.

BACKGROUND OF THE INVENTION

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single cultivar or hybrid an improved combination of desirable traits from the parental germplasm. These important traits may include fresh pod yield, higher seed yield, resistance to diseases and insects, better stems and roots, tolerance to drought and heat, and better agronomic quality. With mechanical harvesting of many crops, uniformity of plant characteristics such as germination and stand establishment, growth rate, maturity and plant height is important.

Choice of breeding or selection methods depends on the mode of plant reproduction, the heritability of the trait(s) being improved, and the type of cultivar used commercially (e.g., F1 hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended etc.).

Promising advanced breeding lines are thoroughly tested and compared to appropriate standards in environments representative of the commercial target area(s) for at least three years. The best lines are candidates for new commercial cultivars; those still deficient in a few traits are used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior garden bean cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line. Each year, the plant breeder selects the germplasm to advance to the next generation. This germplasm is grown under unique and different geographical, climatic and soil conditions, and further selections are then made, during and at the end of the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior garden bean cultivars.

The development of commercial garden bean cultivars requires the development of garden bean varieties, the crossing of these varieties, and the evaluation of the crosses. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the progeny from these crosses are evaluated to determine which have commercial potential as a new cultivar.

Pedigree breeding is used commonly for the improvement of self-pollinating crops or inbred lines of cross-pollinating crops. Two parents that possess favorable, complementary traits are crossed to produce an F1. An F2 population is produced by selfing one or several F1's or by intercrossing two F1's (sib mating). Selection of the best individuals is usually begun in the F2 population; then, beginning in the F3, the best individuals in the best families are selected. Replicated testing of families, or hybrid combinations involving individuals of these families, often follows in the F4 generation to improve the effectiveness of selection for traits with low heritability. At an advanced stage of inbreeding (i.e., F6 and F7), the best lines or mixtures of phenotypically similar lines are tested for potential release as new cultivars. Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

Descriptions of other breeding methods that are commonly used for different traits and crops can be found in one of several reference books (e.g., "Principles of Plant Breeding" John Wiley and Son, pp. 115-161, 1960; Allard, 1960; Simmonds, 1979; Sneep et al., 1979; Fehr, 1987). Proper testing should detect any major faults and establish the level of superiority or improvement over current cultivars. In addition to showing superior performance, there must be a demand for a new cultivar that is compatible with industry standards or which creates a new market. The introduction of a new cultivar may incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Garden bean, *Phaseolus vulgaris* L., is an important and valuable vegetable crop. Thus, a continuing goal of plant breeders is to develop stable, high yielding garden bean cultivars that are agronomically sound. The reasons for this goal are obviously to maximize the amount of yield produced on the land. To accomplish this goal, the garden bean breeder must select and develop garden bean plants that have the traits that result in superior cultivars.

SUMMARY OF THE INVENTION

According to the invention, there is provided a novel garden bean cultivar, designated SB4474. This invention thus relates to the seeds of garden bean cultivar SB4474, to the plants of garden bean cultivar SB4474 and parts thereof, for example pollen, ovule or pod, and to methods for producing a garden bean plant produced by crossing the garden bean SB4474 with itself or another garden bean line, and to methods for producing a garden bean plant containing in its genetic material one or more transgenes and to the transgenic garden bean plants produced by that method. This invention also relates to methods for producing other garden bean cultivars derived from garden bean cultivar SB4474 and to the garden bean cultivar derived by the use of those methods. This invention further relates to hybrid garden bean seeds and plants produced by crossing the line SB4474 with another garden bean line.

The invention is also directed to a method of producing a pod comprising growing a plant according to the instant invention to produce a pod, and harvesting said pod. In one embodiment, the method further comprises processing said pod to obtain a bean product. In one embodiment, a bean product according the instant invention is a fresh produce, a canned product or a frozen product.

The invention is also directed to a method of producing a berry comprising obtaining a pod of a plant according to the instant invention and processing the pod to obtain a berry. In one embodiment, a berry according the instant invention is a fresh product, a canned product or a frozen product.

In another aspect, the present invention provides regenerable cells for use in tissue culture of garden bean cultivar SB4474. The tissue culture will preferably be capable of regenerating plants having the physiological and morphological characteristics of the foregoing garden bean plant, and of regenerating plants having substantially the same genotype as the foregoing garden bean plant. Preferably, the regenerable cells in such tissue cultures will be embryos, protoplasts, seeds, callus, pollen, leaves, anthers, roots, and meristematic cells. Still further, the present invention provides garden bean plants regenerated from the tissue cultures of the invention.

Another objective of the invention is to provide methods for producing other garden bean plants derived from garden bean cultivar SB4474. Garden bean cultivars derived by the use of those methods are also part of the invention.

The invention also relates to methods for producing a garden bean plant containing in its genetic material one or more transgenes and to the transgenic garden bean plant produced by that method.

In another aspect, the present invention provides for single gene converted plants of SB4474. The single transferred gene may preferably be a dominant or recessive allele. Preferably, the single transferred gene will confer such trait as male sterility, herbicide resistance, insect resistance, resistance for bacterial, fungal, or viral disease, male fertility, enhanced nutritional quality and industrial usage. The single gene may be a naturally occurring garden bean gene or a transgene introduced through genetic engineering techniques.

The invention further provides methods for developing a garden bean plant in a garden bean plant breeding program using plant breeding technique including recurrent selection, backcrossing, pedigree breeding, restriction fragment length polymorphism enhanced selection, genetic marker enhanced selection and transformation. Seeds, garden bean plant, and parts thereof produced by such breeding methods are also part of the invention.

DEFINITIONS

In the description and tables, which follow, a number of terms are used. In order to provide a clear and consistent understanding of the specification and claims, including the scope to be given such terms, the following definitions are provided:

"Allele"—The allele is any of one or more alternative form of a gene, all of which alleles relates to one trait or characteristic. In a diploid cell or organism, the two alleles of a given gene occupy corresponding loci on a pair of homologous chromosomes.

"Backcrossing"—Backcrossing is a process in which a breeder repeatedly crosses hybrid progeny back to one of the parents, for example, a first generation hybrid F1 with one of the parental genotype of the F1 hybrid.

"Essentially all the physiological and morphological characteristics"—A plant having essentially all the physiological and morphological characteristics means a plant having the physiological and morphological characteristics, except for the characteristics derived from the converted gene.

"Regeneration"—Regeneration refers to the development of a plant from tissue culture.

"Single gene converted"—Single gene converted or conversion plant refers to plants which are developed by a plant breeding technique called backcrossing wherein essentially all of the desired morphological and physiological characteristics of a line are recovered in addition to the single gene transferred into the line via the backcrossing technique or via genetic engineering.

"Maturity Date"—Plants are considered mature when the pods have reached their maximum desirable seed size and sieve size for the specific use intended.

"Determinate Plant"—a determinate plant will grow to a fixed number of nodes while an indeterminate plant will continue to grow during the season. They have a high pod to vine weight ratio.

"Sieve Size" (sv)—Sieve size measures the diameter of the fresh pod and is used in grading beans. Sieve size 1 means pods that fall through a sieve grader which culls out pod diameters of 4.76 mm through 5.76 mm. Sieve size 2 means pods that fall through a sieve grader which culls out pod diameters of 5.76 mm through 7.34 mm. Sieve size 3 means pods that fall through a sieve grader which culls out pod diameters of 7.34 mm through 8.34 mm. Sieve size 4 means pods that fall through a sieve grader which culls out pod diameters of 8.34 mm through 9.53 mm. Sieve size 5 means pods that fall through a sieve grader which culls out pod diameters of 9.53 mm through 10.72 mm. Sieve size 6 means pods that fall through a sieve grader that will cull out pod diameters of 10.72 mm or larger.

"Garden bean Yield" (Tons/Acre)—The yield in tons/acre is the actual yield of the garden beans at harvest.

"Plant Height"—Plant height is taken from the top of soil to top most leaf of the plant and is measured in centimeters.

"Field holding ability"—A bean plant that has field holding ability means a plant having pods which remain smooth and retain their color even after the seed is almost fully developed.

"Machine harvestable plant"—A machine harvestable bush means a bean plant that stands with pods off the ground. The pods can be removed by a machine from the plant without leaves and other plant parts being harvested.

"Plant adaptability"—A plant having a good plant adaptability means a plant that will perform well in different growing conditions and seasons.

"Nodes to 1$^{st}$ flower"—This is obtained by counting the node above the point of cotyledon attachment to the node from which the first peduncle arises.

"Peduncle"—A peduncle is the stalk that bears flower(s) and subsequent pod(s) arising from a node.

"Node"—A node is the thickened enlargement on a plant. It is where the stipules, leaf and peduncle arise.

"RHS"—RHS refers to the Royal Horticultural Society of England which publishes an official botanical color chart quantitatively identifying colors according to a defined numbering system, The chart may be purchased from Royal Hort Society Enterprise Ltd RHS Garden; Wisley, Woking; Surrey GU236QB, UK.

"Munsell Color Chart—Munsell Color chart is an alternate botanical color chart quantitatively identifying color according to a defined numbering system. It may be purchased through APEDX, 432 Steelhead Way, Boise, Id. 83704 USA.

DETAILED DESCRIPTION OF THE INVENTION

According to the invention, there is provided a novel bean cultivar designated SB4474 and also being referred to herein as 'Ambition'. The garden bean cultivar Ambition originated from a hand-pollinated cross between two Syngenta Seeds, Inc., breeding lines; RB7205-B-2-B5-1- and RB7262-B-1-.

The pedigree method of selection was used in generations F2 through F4 in order to accumulate the traits of smaller, darker pods, stress tolerance and yield. In 2007, a single plant selection was made from the F5 population, and the F6 and F7 generations were bulk harvested to increase seed. Ambition has been uniform and genetically stable for four generations of increases, and is free of off-types and variants.

Garden bean cultivar Ambition is a bush snap bean suitable for the fresh market and can be compared to the variety Caprice from Harris-Moran Seed Company, but the varieties differ significantly when the number of seeds per pod at the four sieve stage are compared. In two different locations grown in Nampa, Id., during the 2010 season, Ambition averaged 7.225 seeds per pod, while Caprice averaged 6.05 seeds per pod. These averages were collected from 20 plants taken from each of the two locations. The previous statements are supported by the statistical analyses shown in Tables 1 and 2. Additionally, when the average weight per 100 seeds is measured, 100 seeds of Ambition weigh approximately 27 grams while 100 seeds of Caprice weigh approximately 31 grams.

The plant height of Ambition is approximately 39 cm and the pods reach edible maturity in approximately 61 days (in Idaho). The bush width is about 40 cm and is of a wide bush form. Pod position is relatively high. Leaf size of Ambition is medium and their color is dark green. The color of the flower standard, wings, and keel is white, and Ambition reaches 50% in 40 days (in Idaho). Pods are dark green and the cross section is round in shape. The spur length of the pods is 8 mm and there is an average of 7 seeds per pod. Sieve distribution of Ambition (from the two locations in Nampa, Id.) is as follows; 34% 3-sieve, 63% 4-sieve, and 3% 5-sieve. Dry seed color is white with a semi-shiny seed coat luster. A hilar ring is present and its color is buff.

This invention also is directed to methods for producing a garden bean plant by crossing a first parent garden bean plant with a second parent garden bean plant wherein either the first or second parent garden bean plant is a garden bean plant of the S64474 line. Still further, this invention also is directed to methods for producing a cultivar SB4474-derived garden bean plant by crossing cultivar SB4474 with a second garden bean plant and growing the progeny seed, and repeating the crossing and growing steps with the cultivar SB4474-derived plant from 0 to 7 times. Thus, any such methods using the cultivar SB4474 are part of this invention: selfing, backcrosses, hybrid production, crosses to populations, and the like. All plants produced using cultivar SB4474 as a parent are within the scope of this invention, including plants derived from cultivar SB4474. Advantageously, the cultivar is used in crosses with other, different, cultivars to produce first generation (F1) garden bean seeds and plants with superior characteristics.

As used herein, the term plant includes plant cells, plant protoplasts, plant cell tissue cultures from which garden bean plants can be regenerated, plant calli, plant clumps and plant cells that are intact in plants or parts of plants, such as embryos, pollen, ovules, flowers, seeds, pods, stems, roots, anthers, and the like.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed garden bean plants, using transformation methods as described below to incorporate transgenes into the genetic material of the garden bean plant(s).

Expression Vectors for Bean Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., Proc. Natl. Acad. Sci. U.S.A., 80:4803 (1983), Aragao F. J. L., et al., Molecular Breeding 4:6 491-499 (1998). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986).

Other selectable marker genes confer resistance to herbicides such as glyphosate, glufosinate or broxynil. Comai et al., Nature 317:741-744 (1985), Gordon-Kamm et al., Plant Cell 2:603-618 (1990) and Stalker et al., Science 242:419-423 (1988), Saker M. M., et al, Biologia Plantarum 40:4 507-514 (1998), Russel, D. R., et al, Plant Cell Report 12:3 165-169 (1993).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), alpha-galactosidase, luciferase and chloramphenicol, acetyltransferase. Jefferson, R. A., Plant Mol. Biol. Rep. 5:387 (1987), Teeri et al., EMBO J. 8:343 (1989), Koncz et al., Proc. Natl. Acad. Sci U.S.A. 84:131 (1987), DeBlock et al., EMBO J. 3:1681 (1984), Grossi M. F., et al., Plant Science 103 :2 189-198 (1994), Lewis M. E., Journal of the American Society for Horticultural Science 119:2 361-366 (1994), Zhang et al., Journal of the American Society for Horticultural Science 122:3 300-305 (1997).

Recently, in vivo methods for visualizing GUS activity that do not require destruction of plant tissue have been made available. Molecular Probes publication 2908, lmagene Green_, p. 1-4 (1993) and Naleway et al., J. Cell Biol. 115: 151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., Science 263: 802 (1994). GFP and mutants of GFP may be used as screenable markers.

Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in garden bean. Optionally, the inducible promoter is operably linked to a nucleotide sequence encoding a signal sequence which is operably linked to a gene for expression in garden bean. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Meft et al., PNAS 90:4567-4571 (1993)); Int gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227: 229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88:0421 (1991).

B. Constitutive Promoters

A constitutive promoter is operably linked to a gene for expression in garden bean or the constitutive promoter is operably linked to a nucleotide sequence encoding a signal sequence which is operably linked to a gene for expression in garden bean.

Many different constitutive promoters can be utilized in the instant invention. Exemplary constitutive promoters include, but are not limited to, the promoters from plant viruses such as the 35S promoter from CaMV (Odell et al., Nature 313:810-812 (1985), Aragao et al., Genetics and Molecular Biology 22:3, 445-449 (1999) and the promoters from such genes as rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)).

The ALS promoter, Xba1/Ncol fragment 5' to the Brassica napus ALS3 structural gene (or a nucleotide sequence similarity to said Xba1/Ncol fragment), represents a particularly useful constitutive promoter. See PCT application WO96/30530.

C. Tissue-specific or Tissue-preferred Promoters

A tissue-specific promoter is operably linked to a gene for expression in garden bean. Optionally, the tissue-specific promoter is operably linked to a nucleotide sequence encoding a signal sequence which is operably linked to a gene for expression in garden bean. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., Science 23:476-482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11): 2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Close, P. S., Master's Thesis, Iowa State University (1993), Knox, C., et al., "Structure and Organization of Two Divergent Alpha-Amylase Genes from Barley", Plant Mol. Biol. 9:3-17 (1987), Lerner et al., Plant Physiol. 91:124-129 (1989), Fontes et al., Plant Cell 3:483-496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., A short amino acid sequence able to specify nuclear location, Cell 39:499-509 (1984), Steifel, et al., Expression of a maize cell wall hydroxyproline-rich glycoprotein gene in early leaf and root vascular differentiation, Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is garden bean. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode Enzymes, Peptides, etc.
   A. Plant disease resistance genes. Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. Tomato encodes a protein kinase); Mindrinos et al., Cell 78:1089 (1994) (Arabidopsis RSP2 gene for resistance to *Pseudomonas syingae*).
   B. A *Bacillus thuringiensis* protein, a derivative thereof or a synthetic polypeptide modeled thereon. See, for example, Geiser et al., Gene 48:109 (1986), who disclose the cloning and nucleotide sequence of a Bt delta-endotoxin gene. Moreover, DNA molecules encoding delta-endotoxin genes can be purchased from American Type Culture Collection, Manassas, Va., for example, under ATCC Accession Nos. 40098, 67136, 31995 and 31998.
   C. A lectin. See, for example, the disclose by Van Damme et al., Plant Molec. Biol. 24:25 (1994), who disclose the nucleotide sequences of several *Clivia miniata* mannose-binding lectin genes.
   D. A vitamin-binding protein such as avidin. See PCT application US93/06487, the contents of which are hereby incorporated by reference. The application teaches the use of avidin and avidin homologues as larvicides against insect pests.
   E. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* alpha-amylase inhibitor).
   F. An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.
   G. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.
   H. An insect-specific venom produced in nature by a snake, a wasp, etc. For example, see Pang et al., Gene 116:165 (1992), for disclosure of heterologous expression in plants of a gene coding for a scorpion insectotoxic peptide.
   I. An enzyme responsible for a hyper accumulation of a monterpene, a sesquiterpene, a steroid, hydroxamic acid, a phenylpropanoid derivative or another non-protein molecule with insecticidal activity.
   J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.
   K. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.
   L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.
   M. A membrane permease, a channel former or a channel blocker. For example, see the disclosure of Jaynes et al., Plant Sci 89:43 (1993), of heterologous expression of a cecropin-beta, lytic peptide analog to render transgenic tobacco plants resistant to *Pseudomonas solanacearum*.
   N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.
   O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Intl Symposium on Molecular Plant-Microbe Interactions (Edinburgh, Scotland) (1994) (enzymatic inactivation in transgenic tobacco via production of single-chain antibody fragments).
   P. A virus-specific antibody. See, for example, Tavladoraki et al., Nature 366:469 (1993), who show that transgenic plants expressing recombinant antibody genes are protected from virus attack.
   Q. A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).
   R. A development-arrestive protein produced in nature by a plant. For example, Logemann et al., Biol/Technology 10:305 (1992), have shown that transgenic plants expressing the barley ribosome-inactivating gene have an increased resistance to fungal disease.

2. Genes that Confer Resistance to a Herbicide, for Example
A. A herbicide that inhibits the growing point or meristem, such as an imidazalinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.
B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. See also Russel, D. R., et al, Plant Cell Report 12:3 165-169 (1993). The nucleotide sequence of a phosphinothricin-acetyl-transferase gene is provided in European application No. 0 242 246 to Leemans et al., DeGreef et al., Bio/Technology 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-52 and Acc1-S3 genes described by Marshall et al., Theor. Appl. Genet. 83:435 (1992).
C. A herbicide that inhibits photosynthesis, such as a triazine (psbA and gs+ genes) and a benzonitrile (nitrilase gene). Przibilla et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).
3. Genes That Confer or Contribute to a Value-Added Trait, Such as
A. Delayed and attenuated symptoms to Bean Golden Mosaic Geminivirus (BGMV), for example by transforming a plant with antisense genes from the Brazilian BGMV. See Arago et al., Molecular Breeding. 1998, 4: 6, 491-499.
B. Increased the pea content in Methionine by introducing a transgene coding for a Methionine rich storage albumin (2S-albumin) from the Brazil nut as described in Arago et al., Genetics and Molecular Biology. 1999, 22: 3, 445-449.

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of Agrobacterium. See, for example, Horsch et al., Science 227:1229 (1985). McClean, P., et al. Plant Cell Tissue Org. Cult. 24(2, February), 131-138 (1991), Lewis et al., Journal of the American Society for Horticultural Science, 119:2, 361-366 (1994), Zhang, Z., et al. J. Amer. Soc. Hort. Sci. 122(3): 300-305 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,591,616 issued Jan. 7, 1997.

B. Direct Gene Transfer

Despite the fact the host range for *Agrobacterium*-mediated transformation is broad, some major cereal or vegetable crop species and gymnosperms have generally been recalcitrant to this mode of gene transfer, even though some success has recently been achieved in rice and corn. Hiei et al., The Plant Journal 6:271-282 (1994) and U.S. Pat. No. 5,591,616 issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 im. The expression vector is introduced into plant tissues with a biolistic device that accelerates the microprojectiles to speeds of 300 to 600 m/s which is sufficient to penetrate plant cell walls and membranes. Russell, D. R., et al. Pl. Cell. Rep. 12(3, January), 165-169 (1993), Aragao, F. J. L., et al. Plant Mol. Biol. 20(2, October), 357-359 (1992), Aragao Theor. Appl. Genet. 93:142-150 (1996), Kim, J.; Minamikawa, T. Plant Science 117: 131-138 (1996), Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992)

Another method for physical delivery of DNA to plants is sonication of target cells. Zhang et al., Bio/Technology 9:996 (1991). Alternatively, liposome or spheroplast fusion have been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-ornithine have also been reported. Hain et al., Mol. Gen. Genet. 199:161 (1985) and Draperetal., Plant Cell Physiol. 23:451 (1982). Electroporation of protoplasts and whole cells and tissues have also been described. Saker, M.; Kuhne, T. Biologia Plantarum 40(4): 507-514 (1997/98), Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994).

Following transformation of garden bean target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic garden bean line. Alternatively, a genetic trait which has been engineered into a particular garden bean cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term garden bean plant, cultivar or garden bean line is used in the context of the present invention, this also includes any single gene conversions of that cultivar or line. The term single gene converted plant as used herein refers to those garden bean plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term backcrossing as used herein refers to the repeated crossing of a hybrid progeny back to one of the parental garden bean plants for that line. The parental garden bean plant which contributes the gene for the desired characteristic is termed the nonrecurrent or donor parent. This terminology refers to the fact that the nonrecurrent parent is used one time in the backcross protocol and therefore does not recur. The parental garden bean plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a garden bean plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic, examples of these traits include but are not limited to, herbicide resistance (such as bar or pat genes), resistance for bacterial, fungal, or viral disease such as gene I used for BCMV resistance), insect resistance, enhanced nutritional quality (such as 2s albumine gene), industrial usage, agronomic qualities such as the "persistent green gene", yield stability and yield enhancement. These genes are generally inherited through the nucleus. Some other single gene traits are described in U.S. Pat. Nos. 5,777,196; 5,948,957 and 5,969,212, the disclosures of which are specifically hereby incorporated by reference.

EXAMPLES

Tables
In the tables 1-2 that follow, the traits and characteristics of garden bean cultivar Ambition are detailed along with corresponding data from the commercial garden bean cultivar 'Caprice,' which was used for comparison.
Explanation of the Statistical Variables Used in the Following Tables 1-2:
AMB_sdspod1=Ambition, Number of seeds/pod at 4-sieve, Plot #1, Nampa, Id., 2010
CAP_sdspod1=Caprice, Number of seeds/pod at 4-sieve, Plot #1, Nampa, Id., 2010
AMB_sdspod2=Ambition, Number of seeds/pod at 4-sieve, Plot #2, Nampa, Id., 2010
CAP_sdspod2=Caprice, Number of seeds/pod at 4-sieve, Plot #2, Nampa, Id., 2010

TABLE 1

Seeds/Pod @ 4 sieve - Plot #1 - Nampa, Idaho, 2009

Descriptive Statistics

| Variable | N | Mean | SD | Minimum | Maximum |
|---|---|---|---|---|---|
| AMB_sdspod1 | 20 | 7.2500 | 0.7864 | 6.0000 | 8.0000 |
| CAP_sdspod1 | 20 | 5.5500 | 0.8256 | 4.0000 | 7.0000 |

TABLE 1-continued

Seeds/Pod @ 4 sieve - Plot #1 - Nampa, Idaho, 2009

One-Way AOV for: AMB_sdspod1 CAP_sdspod1

| Source | DF | SS | MS | F | P |
|---|---|---|---|---|---|
| Between | 1 | 28.9000 | 28.9000 | 44.46 | 0.0000 |
| Within | 38 | 24.7000 | 0.6500 | | |
| Total | 39 | 53.6000 | | | |

Grand Mean 6.4000    CV 12.60

| Homogeneity of Variances | F | P |
|---|---|---|
| Levene's Test | 0.07 | 0.7885 |
| O'Brien's Test | 0.07 | 0.7941 |
| Brown and Forsythe Test | 0.00 | 1.0000 |

Welch's Test for Mean Differences

| Source | DF | F | P |
|---|---|---|---|
| Between | 1.0 | 44.46 | 0.0000 |
| Within | 37.9 | | |
| Component of variance for between groups | | 1.41250 | |
| Effective cell size | | 20.0 | |

| Variable | Mean |
|---|---|
| AMB_sdspod1 | 7.2500 |
| CAP_sdspod1 | 5.5500 |
| Observations per Mean | 20 |
| Standard Error of a Mean | 0.1803 |
| Std Error (Diff of 2 Means) | 0.2550 |

LSD All-Pairwise Comparisons Test

| Variable | Mean | Homogeneous Groups |
|---|---|---|
| AMB_sdspod1 | 7.2500 | A |
| CAP_sdspod1 | 5.5500 | B |
| Alpha | 0.05 | Standard Error for Comparison 0.2550 |
| Critical T Value | 2.024 | Critical Value for Comparison 0.5161 |

All 2 means are significantly different from one another.

TABLE 2

Seeds/Pod @ 4 sieve - Plot #2 - Nampa, Idaho, 2010

Descriptive Statistics

| | AMB_SDSPOD2 | CAP_SDSPOD2 |
|---|---|---|
| N | 20 | 20 |
| Mean | 7.2000 | 6.5500 |
| SD | 1.0052 | 0.6863 |
| C.V. | 13.962 | 10.478 |
| Minimum | 5.0000 | 5.0000 |
| Maximum | 9.0000 | 7.0000 |

One-Way AOV for: AMB_SDSPOD2 CAP_SDSPOD2

| Source | DF | SS | MS | F | P |
|---|---|---|---|---|---|
| Between | 1 | 4.2250 | 4.22500 | 5.70 | 0.0220 |
| Within | 38 | 28.1500 | 0.74079 | | |
| Total | 39 | 32.3750 | | | |

Grand Mean 6.8750    CV 12.52

| Homogeneity of Variances | F | P |
|---|---|---|
| Levene's Test | 2.80 | 0.1023 |
| O'Brien's Test | 2.65 | 0.1116 |
| Brown and Forsythe Test | 2.88 | 0.0977 |

TABLE 2-continued

Seeds/Pod @ 4 sieve - Plot #2 - Nampa, Idaho, 2010

Welch's Test for Mean Differences

| Source | DF | F | P |
|---|---|---|---|
| Between | 1.0 | 5.70 | 0.0227 |
| Within | 33.6 | | |
| Component of variance for between groups | | 0.17421 | |
| Effective cell size | | 20.0 | |

| Variable | Mean |
|---|---|
| AMB_SDSPOD2 | 7.2000 |
| CAP_SDSPOD2 | 6.5500 |
| Observations per Mean | 20 |
| Standard Error of a Mean | 0.1925 |
| Std Error (Diff of 2 Means) | 0.2722 |

LSD All-Pairwise Comparisons Test

| Variable | | Mean | Homogeneous Groups | |
|---|---|---|---|---|
| AMB_SDSPOD2 | | 7.2000 | A | |
| CAP_SDSPOD2 | | 6.5500 | B | |
| Alpha | 0.05 | Standard Error for Comparison | | 0.2722 |
| Critical T Value | 2.024 | Critical Value for Comparison | | 0.5510 |

All 2 means are significantly different from one another.

TABLE 3

A comparison of chosen characteristics between Ambition and the commercial cultivar 'Caprice'. This data was taken from 2010 plots in Nampa, Idaho.

| | Ambition | Caprice |
|---|---|---|
| Market Maturity | | |
| Days to Edible Pods | 62 | 63 |
| Plant | | |
| Habit | Determinate | Determinate |
| Height (cm) | 38.875 cm | 35.25 cm |
| Plant spread/Width (cm) | 40.4 cm | 31.25 cm |
| Pod Position | scattered | Scattered |
| Bush Form | High | High |
| Leaves | | |
| Surface | Indeterminate | Glossy |
| Size | Medium | Medium |
| Color | Dark Green | Dark green |
| Anthocyanin Pigment (1 = absent; 2 = present) | | |
| Flowers | 1 | 1 |
| Stems | 1 | 1 |
| Pods | 1 | 1 |
| Seeds | 1 | 1 |
| Leaves | 1 | 1 |
| Petioles | 1 | 1 |
| Peduncles | 1 | 1 |
| Nodes | 1 | 1 |
| Flower Color/Days to Bloom | | |
| Color of Standard | White | White |
| Color of wings | White | White |
| Color of Keel | White | White |
| Pods (at edible maturity) | | |
| Exterior Color (fresh) | Dark Green | Dark Green |
| Dry Pod Color | Buckskin | Buckskin |
| Cross Section Pod Shape | Round | Round |
| Crease Back | Absent | Absent |
| Pubescence | Sparse | None |
| Constriction (Interlocular Cavitation) | None | None |
| Spur Length (mm) | 8.41 mm | 8.2 mm |

TABLE 3-continued

A comparison of chosen characteristics between Ambition and the commercial cultivar 'Caprice'. This data was taken from 2010 plots in Nampa, Idaho.

| | Ambition | Caprice |
|---|---|---|
| Fiber | Sparse | Sparse |
| Number of seeds/pod | 7 | 6 |
| Suture String | Absent | Absent |
| Seed Development | Slow | Slow |
| Machine Harvest | Adapted | Adapted |
| Percent sieve size distribution at optimum maturity for not-flat pods | | |
| 4.76 to 5.76 mm | 0% | 0% |
| 5.76 to 7.34 mm | 0% | 0% |
| 7.34 to 8.34 mm | 31.85% | 9.50% |
| 8.34 to 9.53 mm | 64.60% | 69.00% |
| 9.53 to 10.72 mm | 3.54% | 13.90% |
| >10.72 mm | 0% | 1.51% |
| 3 seive: | 12 cm length, 8 mm width, 8 mm thickness | 12 cm length, 8 mm width, 8 mm thickness |
| 4 seive: | 13 cm length, 9 mm width, 9 mm thickness | 13 cm length, 8 mm width, 8 mm thickness |
| 5 seive: | 14 cm length, 9 mm width, 9 mm thickness | 14 cm length, 9 mm width, 9 mm thickness |
| Seed Color | | |
| Seed Coat Luster | Semishiny | Dull |
| Seed Coat | Monocrom | Monochrome |
| Primary Color | Grey Green | Grey green |
| Seed Coat Pattern | Solid | Solid |
| Hilar Ring | Present | Present |
| Hilar Ring Color | Buff | Buff |
| Seed Shape and Size | | |
| Hilum View | Elliptical | Elliptical |
| Cross Section | Oval | oval |
| Side View | Oval | oval |
| grams/100 seeds | 27.24 g | 30.88 g |

Deposit

Deposit Information

Applicants have made a deposit of at least 2500 seeds of the garden bean cultivar designated SB4474 with the American Type Culture Collection (ATCC), Manassas, Va., 20110-2209 U.S.A., ATCC Deposit No: PTA-11757. This deposit of the garden bean cultivar designated SB4474 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801-1.809, including providing an indication of the viability of the sample. During the pendency of this application, access to the deposited material will be afforded to the Commissioner on request. All restrictions on the availability of the deposited material from the ATCC to the public will be irrevocably removed upon granting of the patent; however, Applicants have no authority to waive any restrictions imposed by law on the transfer of biological material or its transportation in commerce. Applicants do not waive any infringement of its rights granted under this patent or under the Plant Cultivar Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

All references cited herein are incorporated by reference in the instant application in their entireties.

What is claimed is:

1. Seed of garden bean cultivar designated Ambition, representative seed of said cultivar having been deposited under ATCC Accession No. PTA-11757.

2. A garden bean plant, or a part thereof, produced by growing the seed of claim 1.

3. Pollen of the plant of claim 2.

4. An ovule of the plant of claim 2.

5. A pod or a berry of the plant of claim 2.

6. A tissue culture of regenerable cells of a plant of garden bean cultivar designated Ambition, wherein the tissue regenerates plants having all the morphological and physiological characteristics of a plant of garden bean cultivar designated Ambition, representative seeds having been deposited under ATCC Accession No. PTA-11757.

7. The tissue culture of claim 6, wherein the regenerable cells are produced from protoplasts, calli, meristematic cells, leaves, pollen, embryo, root, root tips, stems, anther, flowers, seeds or pods.

8. A garden bean plant regenerated from the tissue culture of claim 6, wherein the regenerated plant has all the morphological and physiological characteristics of a plant of garden bean cultivar designated Ambition, representative seeds having been deposited under ATCC Accession No. PTA-11757.

9. A method for producing a hybrid garden bean seed comprising crossing a first parent garden bean plant with a second parent garden bean plant and harvesting the resultant hybrid garden bean seed, wherein said first or second parent garden bean plant is the garden bean plant of claim 2.

10. A hybrid garden bean seed produced by the method of claim 9.

11. A method of producing an herbicide resistant garden bean plant comprising transforming the garden bean plant of claim 2 with a transgene that confers herbicide resistance.

12. An herbicide resistant garden bean plant produced by the method of claim 11.

13. The garden bean plant of claim 12, wherein the transgene confers resistance to an herbicide selected from the group consisting of imidazolinone, sulfonylurea glyphosate, glufosinate, L-phosphinothricin, triazine and benzonitrile.

14. A method of producing an insect resistant garden bean plant comprising transforming the garden bean plant of claim 2 with a transgene that confers insect resistance.

15. An insect resistant garden bean plant produced by the method of claim 14.

16. The garden bean plant of claim 15, wherein the transgene encodes a *Bacillus thuringiensis* protein.

17. A method of producing a disease resistant garden bean plant comprising transforming the garden bean plant of claim 2 with a transgene that confers resistance to bacterial, fungal or viral disease.

18. A disease resistant garden bean plant produced by the method of claim 17.

19. A method of producing a garden bean pod comprising:
   a. growing the garden bean plant of claim 2 to produce a garden bean pod, and
   b. harvesting said garden bean pod.

20. The method according to claim 19, further comprising processing said garden bean pod to obtain a seed.

21. The method according to claim 20, wherein said seed is a fresh product, a canned product or a frozen product.

22. A method of producing a seed comprising obtaining a pod of the plant of claim 2 and processing said pod to obtain a seed.

23. The method according to claim 22, wherein said seed is a fresh product, a canned product or a frozen product.

24. The method of claim 9 additionally comprising two or more generations of backcrossing to one of said parent garden bean plants.

* * * * *